United States Patent [19]

Yamamoto et al.

[11] Patent Number: 4,955,890
[45] Date of Patent: Sep. 11, 1990

[54] SURGICAL SKIN INCISION DEVICE, PERCUTANEOUS INFECTION CONTROL KIT AND METHODS OF USE

[75] Inventors: Ronald K. Yamamoto; Stanley R. Conston, both of Redwood City, Calif.

[73] Assignee: Vitaphore Corporation, Menlo Park, Calif.

[21] Appl. No.: 139,505

[22] Filed: Dec. 30, 1987

Related U.S. Application Data

[63] Continuation-in-part of Ser. No. 819,550, Jan. 16, 1986, abandoned.

[51] Int. Cl.⁵ ............................................. A61B 17/32
[52] U.S. Cl. .................................... 606/108; 606/167; 604/175
[58] Field of Search .................. 128/305, 303 R, 311, 128/313, 309, 306; 606/108, 167; 604/175

[56] References Cited

U.S. PATENT DOCUMENTS

| | | |
|---|---|---|
| 3,827,434 | 8/1974 | Thompson et al. . |
| 4,273,128 | 6/1981 | Lary . |
| 4,438,770 | 3/1984 | Unger et al. . |
| 4,461,281 | 7/1984 | Carson . |
| 4,617,738 | 10/1986 | Kopacz ............................. 128/305 |
| 4,619,644 | 10/1986 | Scott . |
| 4,627,436 | 12/1986 | Leckron . |
| 4,633,860 | 1/1987 | Korth et al. . |
| 4,676,782 | 6/1987 | Yamamoto et al. . |

FOREIGN PATENT DOCUMENTS

| | | |
|---|---|---|
| 149537 | 11/1961 | U.S.S.R. . |
| 602175 | 4/1978 | U.S.S.R. . |
| 605610 | 5/1978 | U.S.S.R. . |
| 649423 | 3/1979 | U.S.S.R. . |

*Primary Examiner*—Michael H. Thaler
*Attorney, Agent, or Firm*—Flehr, Hohbach, Test, Albritton & Herbert

[57] ABSTRACT

A surgical cutter device for producing a skin incision of controlled length and depth at a guidewire skin puncture location is described. The cutter is particularly useful for making incisions for the insertion of catheters. In addition, there is described a device which takes full advantage of such precisely formed skin incisions, comprising a subcutaneous cuff for sealing the entrance incision for a catheter and providing antimicrobial action at the sealed entrance, and an introducer for inserting the cuff subcutaneously along the associated catheter. A preferred method for using the cutter, cuff and introducer is also described.

7 Claims, 3 Drawing Sheets

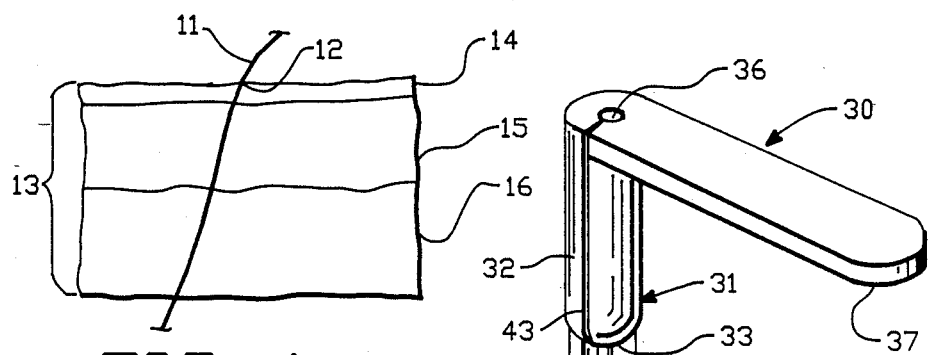
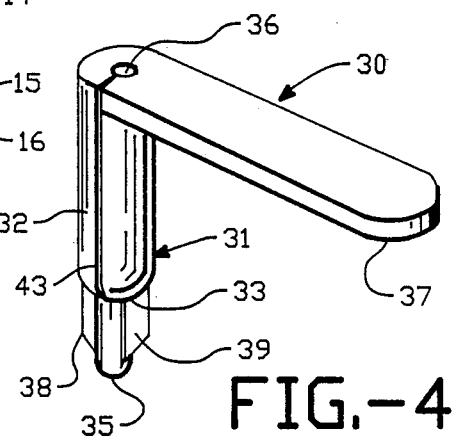
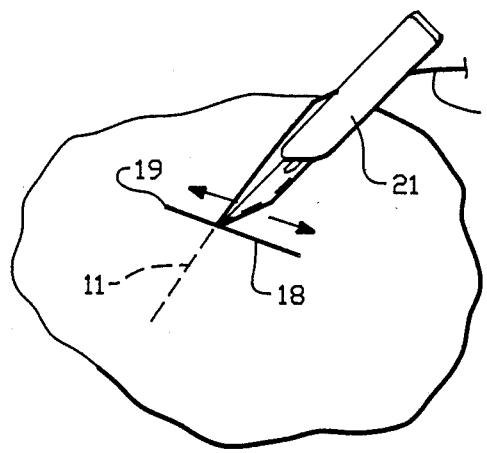
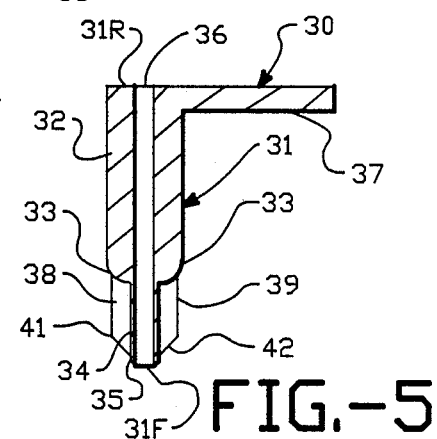
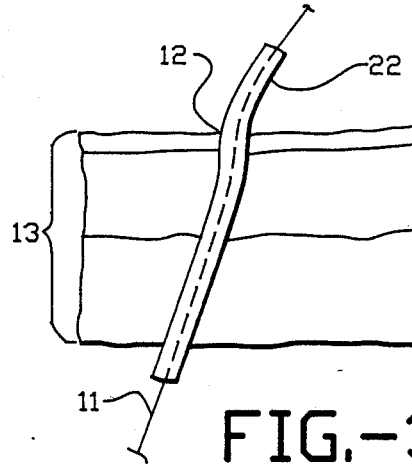
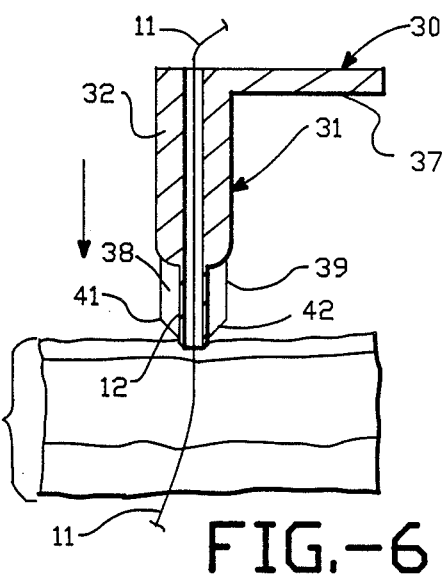

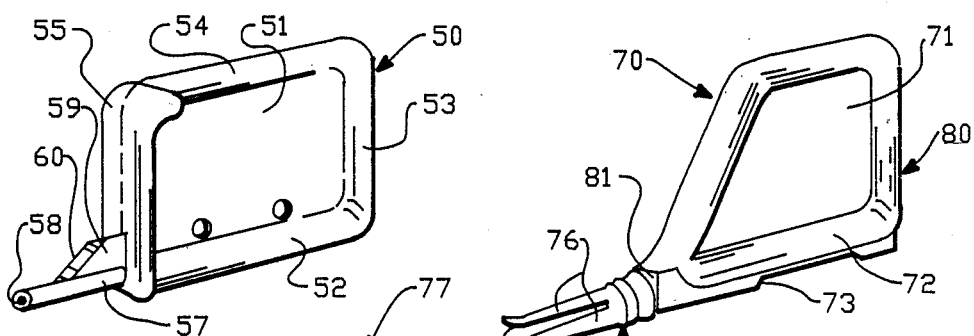
FIG.-7
FIG.-9
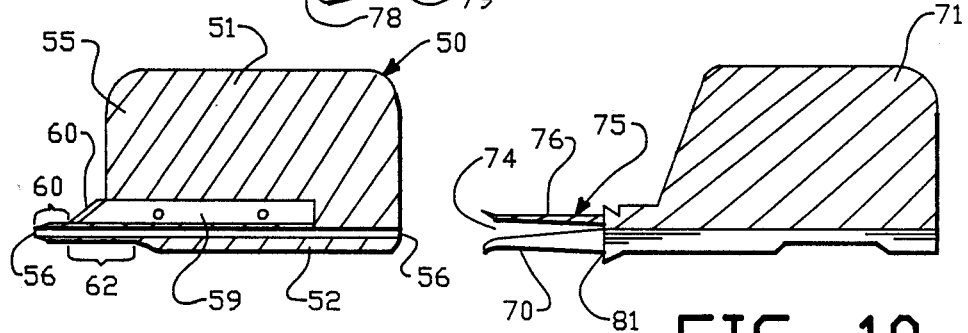
FIG.-8
FIG.-10
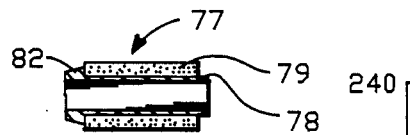
FIG.-11
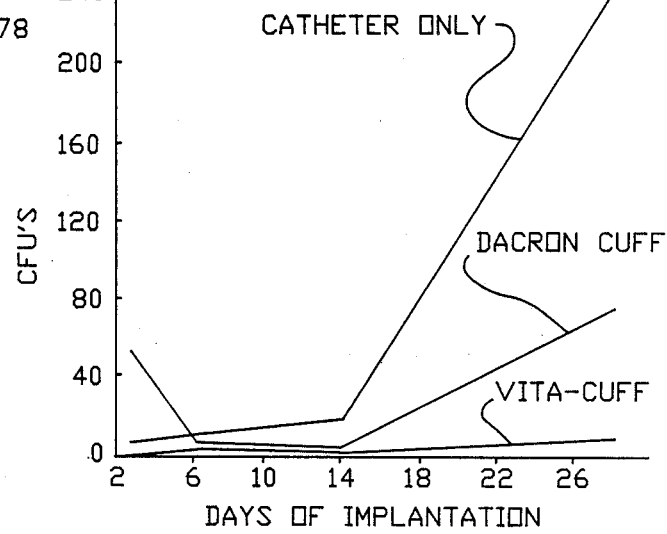
FIG.-15

SURGICAL SKIN INCISION DEVICE, PERCUTANEOUS INFECTION CONTROL KIT AND METHODS OF USE

This is a continuation-in-part application of co-pending U.S. Pat. application Ser. No. 819,550, filed Jan. 16, 1986, now abandoned, for SURGICAL DEVICE FOR FORMING A CONTROLLED SKIN INCISION AROUND A PERCUTANEOUS CONDUIT.

BACKGROUND OF THE INVENTION

The present invention relates to a surgical device for creating precise, small skin incisions for the introduction of a percutaneous conduit. In particular, the invention relates to such a device which is designed for creating a small skin incision of controlled geometry about a puncture created by a guidewire or needle for the purpose of introducing a catheter or other percutaneous conduit. The invention also relates to an antimicrobial cuff for the conduit, to a device for positioning the cuff via the precision incision, and to methods of using the cutter, cuff and introducer.

A percutaneous device or conduit is an implement which passes through the skin, allowing the linkage of an intracorporeal organ or cavity with extracorporeal equipment. There exists a wide variety of clinical applications for percutaneous devices. For example, in the facilitation of fluid transport, percutaneous conduits, or catheters, are used to access blood for dialysis, pressure monitoring, or laboratory diagnosis, to deliver drugs or nutritional solutions, and to drain wound exudate.

In the clinical placement of catheters, it is often necessary to create a small skin incision across the puncture initially created by a needle, to allow the introduction of the larger diameter catheter. The conventional procedure for performing this catheter placement is shown schematically in FIGS. 1 through 3. As shown in FIG. 1, initially the skin 13 is punctured with a guidewire or needle 11, at a desired location 12, and the wire is inserted through the epidermis 14, dermis 15 and subcutaneous tissue 16 to provide intracorporeal access to the deeper tissues.

Then, referring to FIG. 2, two incisions 18 and 19 are made at opposite sides of the guidewire 11. Typically, the two incisions are made with a No. 11 scalpel blade (designated by reference numeral 21) or an equivalent device by placing the non-cutting edge against the guidewire 11 and cutting outwardly from the wire, then repeating the operation in the opposite direction. Finally, as shown in FIG. 3, a catheter 22 is inserted along the guidewire 11 through the skin 13 into the deeper tissues.

The skin incision step is of particular relevance to our discussion, and to the present invention, for it is difficult to make a cut of the desired width and depth necessary for introduction of the catheter 22 without forming a cut either greater or smaller than desired. Furthermore, care must be taken not to sever the guidewire when making the skin incision, since the resulting internal piece of wire might then travel harmfully within the vascular system.

U.S. Pat. No. 4,438,770, issued Mar. 27, 1984 to Unger et al discloses a spring-biased skin incising device which is designed to provide an incision of controlled length and depth. To make an incision, the cutter, which is mounted within a support base, is cocked and the base is positioned on the patient's skin at the site of the incision. The cutter is then released and the spring automatically displaces the cutter along a guide slot to make a cut of controlled depth and length. The device provides only a single cut and, thus, would require two cutting operations to make a catheter incision, similar to the situation using a conventional scalpel (see FIG. 2). Furthermore, the cutter is surrounded by the base so that, apparently, it would be impossible to make a cut adjacent the guidewire 11.

SUMMARY OF THE INVENTION

In view of the above discussion, it is an object of the present invention to provide a surgical device which simplifies the above discussed incision procedure and performs one or more cuts as a single step, while ensuring alignment with the catheter puncture, eliminating the guidewire cutting hazard during the incision procedure, and producing a skin incision of controlled geometry (width and depth).

It is also an object to provide an antimicrobial cuff for catheters and other percutaneous conduits.

It is a further object to provide an introducer device for inserting the antimicrobial cuff subcutaneously through the skin incision.

In one aspect, the present invention relates to a cutter device for making skin incisions at a guidewire puncture location, which includes: (a) a handle having a front edge or hilt; (b) a tapered introducer tube which is mounted to and extends forwardly from the front edge of the handle and tapers to a relatively small size at its front end; (c) a longitudinal hole which extends through the handle and introducer tube and has an inner diameter selected for providing a close slidable fit over a guidewire to maintain precise alignment of the cutter device on the guidewire; and (d) at least a single blade mounted along the side of the tube. The blade abuts the front edge or hilt of the handle so that the hilt acts as a stop to selectively limit the depth of cut provided by the cutter device; terminates at a point spaced rearwardly of the front end of the introducer tube; and has a generally forward facing cutting edge which extends generally radially relative to said tube and is of a selected width for providing a cut sized to closely receive a device such as a catheter or anti-bacterial cuff inserted into the skin along the guidewire.

In another aspect, the present invention relates to an antimicrobial cuff assembly and introducer device for depositing the cuff subcutaneously through a skin incision along a percutaneous conduit such as a catheter at a guidewire puncture location. The anti-bacterial cuff assembly includes (a) an anti-bacterial cuff formed of a generally tubular shaped bio-degradable collagen matrix containing an antimicrobial agent and (b) an inner tube or sleeve of silicone elastomer material which slidably supports the antimicrobial cuff and has an inner diameter selected for applying radial compression to a catheter of selected size when inserted therein. The cuff introducer includes (a) a generally flat handle of rectangular configuration or other suitable configuration having a groove along one edge thereof to permit releasably threading a guidewire and selected catheter therethrough; and (b) an introducer tube which extends from the handle. The introducer tube has (1) a bore therethrough aligned with and communicating with the groove for receiving a guidewire and selected catheter, and (2) an outer diameter selected for releasably mounting the antimicrobial cuff assembly thereon.

In still another aspect, the present invention relates to a method for placing an antimicrobial, sealing cuff subcutaneously on a catheter along a guidewire, comprising: providing a cutter device as described above for making skin incisions at a guidewire puncture location; threading the cutter over the guidewire and advancing the cutter against the skin thereby producing an incision of depth predetermined by the position of the hilt relative to the blade and length predetermined by the width of the blade, then withdrawing the cutter over the guidewire; providing an antimicrobial cuff and introducer device as described above; threading a catheter of selected size through the introducer device and the cuff and advancing the catheter subcutaneously over the wire; advancing the introducer along the wire subcutaneously to position the antimicrobial cuff assembly beneath the skin; and separating the introducer from the catheter and cuff by pivoting the catheter and introducer away from one another and withdrawing the introducer from the catheter and cuff.

BRIEF DESCRIPTION OF THE DRAWINGS

The above and other aspects of the invention are described with respect to the drawings, in which:

FIGS. 1 through 3 show a conventional sequence for introducing a catheter or other percutaneous conduit;

FIG. 4 is a perspective view of the surgical device of the present invention;

FIG. 5 is a cross-section view of the device of FIG. 4;

FIG. 6 illustrates the use of the device of FIG. 4.

FIGS. 7 and 8 are, respectively, a perspective view and a vertical cross-section view of a presently preferred embodiment of the surgical cutter device of the present invention;

FIG. 9 is an exploded perspective view of a vertical cross-section view of a presently preferred embodiment of an antimicrobial cuff and an associated cuff introducer;

FIG. 10 is a vertical cross-section view of the introducer of FIG. 9;

FIG. 11 is an enlarged longitudinal cross-section view of the cuff shown in FIG. 9;

FIG. 15 depicts the comparative long term bacteria counts associated with catheters without any cuff, catheters with plain Dacron TM velour cuffs (no antimicrobial action) and catheters protected by antimicrobial cuffs.

DETAILED DESCRIPTION OF THE PREFERRED EMBODIMENTS

Overview

Figure 12:
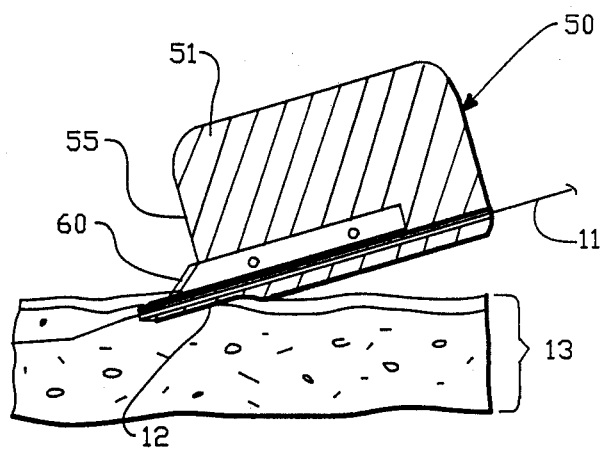
FIG. 12 depicts the use of the cutter shown in FIGS. 7 and 8.

The present invention relates to an improved surgical cutter device for making a controlled cut at a guidewire puncture location to permit the subcutaneous insertion of a device such as a catheter and/or antimicrobial cuff. In addition, the present invention relates to a percutaneous infection-control kit comprising (1) the cutter; (2) a tissue in-growth-promoting antimicrobial cuff which is positioned subcutaneously around a catheter of matching size to seal the introduction incision and prevent infection; and (3) an introducer device for positioning the catheter and associated cuff subcutaneously through the incision made by the cutter. The invention also relates to the method of using the cutter and percutaneous infection-control kit. Described below are preferred and alternative embodiments of the surgical cutter device, the preferred embodiment of the percutaneous infection-control kit and the preferred method of using the cutter and kit. The preferred embodiment of the antimicrobial cuff and introducer described here is an improvement of the cuff and expansion tool-type introducer disclosed in commonly assigned U.S. Pat. No. 4,676,782 which is incorporated by reference herein.

First Cutter Embodiment 30

One embodiment of my invention is illustrated in perspective in FIG. 4 during the process of making a skin incision, and in cross-section in FIG. 5. Referring to those two figures and, in particular, to the components identified by reference numerals in those figures, the surgical device 30 shown there which embodies my present invention is a device for making skin incisions at puncture location 12. The device 30 includes a longitudinal tubular body 31 having opposite longitudinal ends which are arbitrarily designated 31R and 31F in FIG. 5. Typically, the body is formed of a material suitable for injection molding such as polypropylene, polyethylene, or polysulfone. The body 31 includes a first, relatively large diameter section 32 at the first end 31R. Body section 31 is smoothly contoured at 33 into a second, reduced diameter section 34. A longitudinal hole or bore 36 is formed in the body 31 along longitudinal axis 40 for receiving and being guided along a needle or guidewire 11, as shown in FIG. 5. Longitudinal slot 43 extends from the outside of the tubular body 31 to the bore 36 to permit lateral insertion of the bore and the device onto the wire (or needle) 11 and, thus, avoid having to thread the end of the wire through the bore.

Blades 38 and 39 are mounted along the sides of the second tubular body section 34 with their lengths generally parallel to the body axis, i.e., to the bore 36, and their widths (the dimension perpendicular to the length) generally perpendicular to the bore. The blades 38 and 39 include forward facing, radially extending cutting edges 41 and 42. The cutting edges 41 and 42 are angled generally rearwardly from the second body section 34 at an acute angle of about 45° to the second body section 34. Due to the small outer diameter of the body section 34, the forward ends of the cutting blade edges 41, 42 are positioned laterally very close to the bore 36 and to the guidewire 11. This positioning places the two blade incisions closely adjacent to, that is, at, the puncture 12. See FIG. 6.

Typically, the blades 38 and 39 are mounted in a coplanar orientation to produce a straight line slit or incision. However, the blades may be oriented at angles other than 180°, for the purpose of forming angled rather than straight line incisions. In fact, in addition to the preferred two-blade embodiment shown in FIGS. 4 and 5, the blade means may comprise a single blade or a multiplicity of blades.

The tubular body 31 preferably includes a short, third, reduced diameter section 35 at the second, forward end 31F, which extends forward of the blade cutting surfaces 41 and 42 for dilating the skin and protecting the guidewire during the incision process. Finally, the surgical device 30 includes a handle 37 which is attached to or part of the body section 31.

While surgical device 30 can be manufactured in sections and/or using various fabrication techniques, in a presently preferred working embodiment all three body sections 32, 34 and 35 as well as the handle 37 are formed as a unitary, integral molded plastic assembly. The blades 38 and 39 are mounted within slots formed along the intermediate second section 34 which extend into the large body section 32. The blades can be attached to the body 31 as part of, and by, the molding process and/or can be attached by adhesive or by thermocompression bonding.

Referring to FIG. 6, during use of my surgical device 30 to produce a skin incision, the guidewire 11 is inserted through the skin epidermis, dermis and subcutaneous tissue into the deeper tissues. Then, the slot 43 is used to insert the device 30 over the protruding guidewire 11. Using handle 37, the device 30 is moved along the guidewire toward the skin 13 to engage the skin at the guidewire puncture point 12 and then simultaneously produce the two cuts which terminate at the guidewire and puncture. Next, the cutting device 30 is retracted slightly and removed from the guidewire. A catheter or other percutaneous conduit 22 is then inserted along the guidewire and through the incision and the skin 13 into the underlying tissue. As mentioned, the two angled, radial blade cutting edges 41 and 42 facilitate producing a controlled cut at the skin 27. In addition, the small forward tube segment 35 functions to slightly dilate the skin to produce a clean cut while protecting the guidewire from any possible damage.

Presently Preferred Cutter Embodiment 50

Referring to FIGS. 7–9, in a presently preferred embodiment 50, the cutter comprises a generally flat, generally rectangular handle 51, preferably of an inexpensive, easily formed, structurally rigid material, such as plastic, having enlarged peripheral edges, including longitudinal edge 52 and transverse front edge or hilt 55. Alternatively, component 55 can be an integral part of tube 57 or can be a separate component which is mounted on tube 57 and/or handle 51. A longitudinal bore 56 (FIG. 8) is formed in the enlarged edge section 52 and in the introducer tube 57 which extends from the front edge 55 of the handle. The introducer tube 57 tapers slightly from a relatively large outside diameter adjacent hilt 55 to a relatively small outside diameter at tube front end 58. A blade 59 is mounted within the longitudinal edge 52 and along rear section 62 of introducer tube 57 (FIG. 8). As a consequence, the length of the blade is generally parallel to the axis of tube 57 and bore 56 and the blade's width (the dimension perpendicular to the length) is generally perpendicular to the tube. Preferably, the handle 51 is molded about the blade or is formed in mating halves which are joined by adhesive, ultrasonic bonding, etc. The blade 59 includes a generally forward-facing, radially-extending cutting edge 60 which preferably terminates at a point spaced from the front end 58 of the tube 57, so that a tapered front section 61 of the tube (see FIG. 8) extends in front of the cutting edge 60. At the opposite, rearward end, the cutting edge terminates proximate the hilt or stop 55, which limits the depth of cut of the blade. The blade's cutting edge 60 is angled generally rearwardly from the front end thereof at an acute angle of about 45° to the tube axis. Due to the small outer diameter of the tube 57, the forward end of the cutting blade 59 is positioned laterally very close to the bore 56 and the guidewire 11 (see FIG. 9). This positioning places the blade incision closely adjacent to, that is, essentially at, the puncture 12 without risking severing the guidewire.

Although other, typically greater dimensions will be readily derived by those of usual skill in the art, the presently preferred embodiment of the cutter 50 incorporates a forward tube section 61 which is approximately one-eighth inch in length. Also, although two blades 59 or a multiplicity of blades can be used, presently one is preferred because of ease of construction and use and because one blade 59 provides a sufficiently large opening.

In addition, while the cutter 50 is described as having an enclosed longitudinal bore 56, a slot or groove can be provided in the manner of cutter 30, FIG. 4, or introducer 70, FIG. 10, so that the cutter 50 can be readily mounted to and removed from the guidewire, without requiring threading the length of the guidewire. However, any slight inconvenience in threading the cutter is deemed less important than the inherent inability of the non-grooved cutter 50 to inadvertently slip off the guidewire during use.

Referring to FIG. 12, the use of cutter 50 is identical to that of cutter 30, FIG. 4, with the exception that the cutter 50 is threaded along guidewire 11. That is, to produce a skin incision, the guidewire 11 is inserted through the skin epidermis, dermis and subcutaneous tissue into the deeper tissues and, typically, into a vein or artery. Then, the cutter 50 is threaded along the guidewire 11 to engage the skin at the guidewire puncture location 12 and produce the cut which terminates at the guidewire and puncture. Next, the cutting device 50 is retracted along the guidewire 11 and removed. A catheter or other percutaneous conduit can then be inserted along the guidewire and through the incision in the skin into the underlying vein or artery.

The numerous advantages of this relatively simple device include (1) a simplified single incision stroke that provides one, two or more incisions simultaneously in alignment with the guidewire; (2) the elongated introducer tube 57, which ensures precise tracking of the cutter along the guidewire 11 and ensures that the cut is at the desired angle determined by the orientation of the guidewire; (3) the elongated tapered forward introducer end section 61 which stretches and dilates the skin for cutting, thereby providing ease of cutting and a clean cut; (4) the hilt/stop 55 which limits the depth of cut; (5) the blade's cutting edge which determines the length of the cut (the size of the opening), thereby cooperatively ensuring, with the hilt/stop 55, a cut of controlled width and depth which is tailored to the dimensions of the catheter or cuff and which prevents forming a cut greater or smaller than is desired; and (6) the abutting, contiguous hilt 55 and blade 59 and the forward facing cutting edge 60 which eliminate the possibility of cutting the skin (undesirably enlarging the incision) upon retraction of the cutter.

Furthermore, based upon the above disclosure, those of usual skill in the art will be able to derive modifications of my surgical device which are within the scope of the disclosure and the definition of the invention contained in the claims.

Percutaneous Infection-Control Introducer Assembly and Kit

FIGS. 9–11 depict the structure of a preferred embodiment 70 of my anti-bacterial cuff assembly 77 and cuff introducer 80. The introducer 80 comprises a generally flat, substantially rectangular handle having enlarged edges (which facilitate holding the handle), including an enlarged edge 72 having a longitudinal surface slot or groove 73 formed therein for receiving a guidewire, catheter, etc., as described below. The longitudinal slot 73 communicates with a bore or hole 74 formed in a forwardly-extending introducer tube 75. The tube 75 itself comprises a plurality of resilient tongues 76.

The antimicrobial cuff assembly 77 is a cuff 79 formed from an antimicrobial agent-containing collagen matrix or sponge which is supported on an inner silicone sleeve 78. The sleeve is inserted over the outwardly biased tongues 76 of the introducer tube and into abutment against stop 81. An enlarged head 82 (FIG. 11) of the sleeve helps to securely retain the cuff assembly 77 against stop 81 and on the introducer tube 75.

The cuff 79 is designed to provide protection against infections related to percutaneous conduits such as vascular catheters. The cuff assembly 77 is placed around a catheter 22 of matching size (FIG. 13) and is then positioned just beneath the skin using the introducer 80. When the introducer is removed, the cuff 79 applies radial compression to the catheter 22, thus securing itself in place. The outer, tissue-interfacing surface of the cuff assembly reduces the incidence of infection related to percutaneous catheters by two basic mechanisms: (1) by promotion by tissue in-growth into the outer porous matrix of the cuff 79 for creating of a catheter-tissue seal at the skin interface; and (2) by the use of an antimicrobial agent incorporated into the porous cuff matrix. The tissue interfacing aspect of the cuff is provided by the collagen matrix; the antimicrobial activity is provided by an antimicrobial agent such as, preferably, silver ions bonded to the collagen matrix. A preferred method of forming the silver ion containing collagen matrix is described in co-pending Yamamoto U.S. Pat. application Ser. No. 028,645, entitled "Method of Forming Silver Chelated Collagen Having Bactericidal Properties", filed Mar. 20, 1987, which application is hereby incorporated by reference. The antimicrobial activity lasts until the cuff is completely absorbed by the tissue in four to six weeks.

As alluded to above, the cutter 50 and the cuff introducer assembly 70 are useful separately. In addition, as described more fully below, they are especially adapted for cooperative use as the components of a percutaneous infection-control kit. Specifically, the cutter 50 is used to make a precise incision (see FIG. 12) which is used for placement of the cuff assembly 77 subcutaneously using the introducer 80 (see FIGS. 13 and 14).

Cuff Insertion Technique

Figure 13:
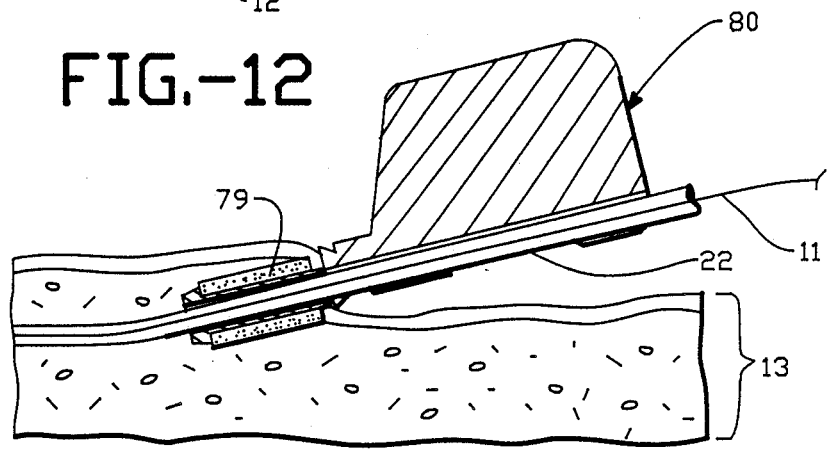
FIGS. 13 and 14 depict the use of the cuff and the cuff introducer shown in FIGS. 9–11.
Figure 14:
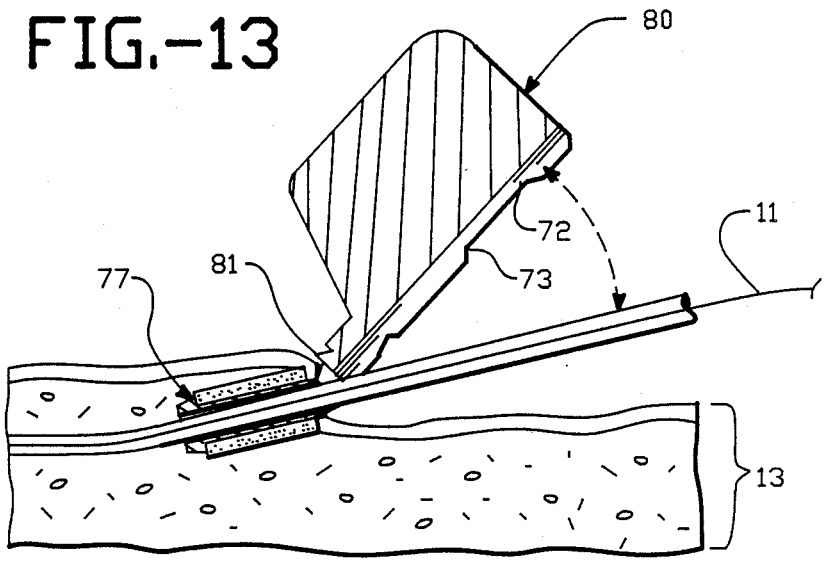

The process of cooperatively using the cutter 50, the introducer 80 and the cuff assembly 77 is depicted sequentially in FIGS. 12-14. Initially, and referring to FIG. 12, using the standard Seldinger technique, the desired vein is located, an insertion needle (not shown) is inserted through the skin and into the desired vein and the spring guidewire 11 is threaded through the insertion needle into the vein and the insertion needle is removed.

Next, and referring further to FIG. 12, the cutter 50 is threaded over the guidewire 11 and advanced into the skin so that the blade 59 produces an incision of the specified size (cutters of different size can be used for different sizes of catheters). The cutter 50 is then withdrawn over guidewire 11 and discarded.

The catheter 22 is then threaded through the introducer 80 and the cuff assembly 77 and is advanced along the wire 11 into the vein, as shown in FIG. 13. Using firm pressure, the introducer 80 is moved forward along the catheter 22 and guidewire 11 to insert the cuff assembly 77 just beneath the skin.

Referring to FIG. 14, the introducer 80 is now separated from the cuff assembly 77 using the illustrated pivotal, wishbone-like action. Finally, the guidewire 11 is removed, the catheter is sutured in place immediately above the insertion site and a syringe or intravenous tubing is attached to the catheter in the conventional manner. The internal diameter of the resilient silicon sleeve 78 has an inside diameter which is slightly smaller than the outside diameter of the associated catheter. Consequently, when the introducer is removed, the cuff assembly applies radial compression to the catheter, thus securing itself in place on the catheter.

The cuff 79 is adhered to the silicone sleeve 78, which also has an inside diameter slightly smaller than the outer diameter of the array of resilient introducer fingers 76 (FIG. 10). As a result, the fingers 76 and the annular shoulder 81 of the handle firmly hold the cuff assembly 77 during insertion. In addition, and as mentioned above, when the introducer 80 is removed, the cuff assembly 77 applies radial compression to the catheter 22, thus securing itself in place on the catheter. After placement, the cuff 79 absorbs physiological fluids, quickly swelling to approximately twice its original size and sealing the incision. As mentioned, the porous collagen matrix promotes tissue in-growth, creating a catheter-tissue seal at the skin interface within a few days and further securing the catheter in place and reducing catheter movement. In addition, the antimicrobial agent provides in vitro antimicrobial activity against microorganisms which commonly cause catheter-related infections in medical facilities.

EXAMPLES

In Vitro Microbiological Activity

The silver ion-impregnated antimicrobial collagen has demonstrated in vitro antimicrobial activity against actual clinical microorganisms which commonly cause catheter-related infections in medical facilities. Representative organisms included nosocomial strains of gram-negative and gram-positive bacteria and yeasts. Test disks made of silver ion-impregnated antimicrobial collagen were placed on agar plates which had been inoculated with different microorganisms. Using standard test procedures, the plates were then incubated and measured for zones of growth inhibition. The following strains of microorganisms were tested:

1. Staphylococcus aureus (ATCC#25923);
2. Escherichia coli (ATCC#25922);
3. Pseudomonas aeruginosa (ATCC#27853);
4. Staphylococcus epidermidis (Clinical isolate);
5. Candida albicans (Clinical isolate); and
6. Klebsiella pneumoniae (Clinical isolate).

In all cases, the silver ion-impregnated antimicrobial collagen test disks demonstrated significant inhibition zones. Inhibition zones occurred even after several transfers of test disks to fresh lawn plates.

In Vivo Activity

Twenty-five rabbits were used in a test designed to measure the safety and efficacy of the antimicrobial cuff of silver ion-impregnated antimicrobial collagen (hereafter, "antimicrobial cuff"), as a percutaneous tissue interfacing device with antimicrobial properties. Four catheters without lumens were implanted into the subcutaneous tissues on each side of the spine of each test rabbit. On one side, antimicrobial cuffs were placed onto all four catheters just below the skin interface. On the other side, two catheters were left without antimicrobial cuffs, and the remaining two catheters had dacron velour cuffs attached. After implantation periods of 3, 7, 14 and 28 days, the catheter segments were removed during sterile necropsy. The catheter segments were cultured according to Maki's semi-quantitative roll techniques. See Maki et al, Semi-quantitative Culture Method for identifying Intravenous-Catheter-Related Infection, NEJM, Vol. 296, No. 23, pp 1305-1309 (1977). No antimicrobial cuff implant site showed macroscopic signs of infection during the course of the study. One animal had catheter bacterial counts greater than 15 CFU's on two antimicrobial cuff sites due to massive infection of the opposing blank catheters and catheters with the dacron velour cuff. Referring to FIG. 15, overall, the average catheter colony counts and the number of catheters with 15 or greater CFU's were reduced by greater than 90 percent relative to the catheter segments used without the antimicrobial cuff devices.

Having thus described preferred and alternative embodiments of the present cutter device, antimicrobial cuff and cuff introducer device and preferred methods of using the cutter alone and in combination with the antimicrobial cuff and cuff introducer, what is claimed is:

1. An antimicrobial cuff and introducer device for depositing the cuff subcutaneously along a catheter at a guidewire puncture location, comprising:
   (A) an anti-bacterial cuff assembly comprising (a) an anti-bacterial cuff formed of a generally tubular bio-degradable collagen matrix containing an antimicrobial agent and (b) an inner tube or sleeve of silicone elastomer material slidably supporting the antimicrobial cuff and having an inner diameter selected for applying radial compression to a catheter of selected size when inserted therein; and
   (B) a cuff introducer comprising (a) a generally flat, generally rectangular handle having a groove along one edge thereof for releasably threading a guidewire and selected catheter therethrough; and (b) an introducer tube extending from the handle and having (1) a bore therethrough aligned with and communicating with the groove for receiving a guidewire and selected catheter, and (2) an outer diameter selected for releasably mounting the antimicrobial cuff assembly thereon;
   (C) whereby (a) threading a catheter through the groove and introducer tube and antimicrobial cuff assembly; (b) threading the catheter, introducer tube and antimicrobial cuff assembly along the guidewire and placing the antimicrobial cuff subcutaneously and (c) retracting the introducer leaves the antimicrobial cuff assembly in place on the catheter, allowing tissue in-growth into the antimicrobial cuff, and (d) subsequent removal of the catheter removes the inner tube therewith.

2. A device according to claim 1 wherein said cuff has tissue in-growth properties.

3. A kit comprising an antimicrobial cuff and components for making a skin incision and subcutaneously inserting a catheter and said antimicrobial cuff along said catheter through said incision, comprising:

(A) a cutter device for making skin incisions at a guidewire puncture location, comprising: (a) a generally flat rectangular handle having a front edge; (b) a tapered introducer tube mounted to and extending forwardly from the front edge of the handle, the introducer tube having a front end and tapering to a smaller outer diameter at the front end; (c) a longitudinal hole extending through the handle and introducer tube and having an inner diameter selected for providing a close slidable fit over a guidewire to maintain precise alignment of the cutter device on the guidewire; and (d) at least a single blade mounted along the side of the tube, the blade (1) abutting the front edge of the handle so that the front edge acts as a stop to selectively limit the depth of cut provided by the cutter device, (2) terminating at a point spaced rearwardly of the front end of the introducer tube and (3) having a generally forward facing cutting edge extending generally radially relative to said tube and being of a selected width for providing a cut sized to closely receive a catheter and cuff inserted into the skin along the guidewire;

(B) an antimicrobial cuff assembly comprising (a) an anti-bacterial cuff formed of a generally tubular bio-degradable collagen matrix containing an antimicrobial agent and (b) an inner tube or sleeve of silicone elastomer material adhered to and supporting the antimicrobial cuff and having an inner diameter selected for applying radial compression to a catheter of selected size when inserted therein; and (C) a cuff introducer comprising (a) a generally flat, generally rectangular handle having a groove along one edge thereof for releasably threading a guidewire and selected catheter therethrough; and (b) an introducer tube extending from the handle and having (1) a bore therethrough aligned with and communicating with the groove for receiving a guidewire and selected catheter, and (2) an outer diameter selected for releasably mounting the antimicrobial cuff assembly thereon;

(C) whereby (a) threading a catheter through the groove and introducer tube and antimicrobial cuff assembly; (b) threading the catheter, introducer tube and antimicrobial cuff assembly along the guidewire and placing the antimicrobial cuff subcutaneously and (c) retracting the introducer leaves the antimicrobial cuff assembly in place on the catheter, allowing tissue in-growth into the antimicrobial cuff, and (d) subsequent removal of the catheter removes the inner tube therewith.

4. A kit according to claim 3 wherein said cuff has tissue in-growth properties.

5. A method for placing an antimicrobial, sealing cuff subcutaneously on a catheter along a guidewire comprising: providing (A) a cutter device for making skin incisions at a guidewire puncture location, comprising: (a) a generally flat handle having a front edge or hilt; (b) a tapered introducer tube mounted to and extending forwardly from the front edge of the handle, the introducer tube having a front end and tapering to a relatively small size at the front end; (c) a longitudinal hole extending through the handle and introducer tube and having an inner diameter selected for providing a close slidable fit over a guidewire to maintain precise alignment of the cutter device on the guidewire; and (d) at least a single blade mounted along the side of the tube, the blade (1) abutting the front edge of the handle so that the front edge acts as a stop to selectively limit the depth of cut provided by the cutter device, (2) terminating at a point spaced rearwardly of the front end of the introducer tube and (3) having a generally forward facing cutting edge extending generally radially relative to said tube and being of a selected width for providing a cut sized to closely receive a device such as a catheter or anti-bacterial cuff inserted into the skin along the guidewire;

threading the cutter over the guidewire and advancing the cuter against the skin thereby producing an incision of depth predetermined by the position of the hilt relative to the blade and length predetermined by the width of the blade, then withdrawing the cutter over the guidewire;

providing an antimicrobial cuff and introducer device for depositing the cuff subcutaneously along the catheter at the guidewire puncture location, comprising (B) an anti-bacterial cuff assembly comprising (a) an anti-bacterial cuff formed of a generally tubular bio-degradable collagen matrix containing an antimicrobial agent and (b) an inner tube or sleeve of silicone elastomer material slidably supporting the antimicrobial cuff and having an inner diameter selected for applying radial compression to a catheter of selected size when inserted therein; and (C) a cuff introducer comprising (a) a generally flat, generally rectangular handle having a groove along one edge thereof for releasably threading a guidewire and selected catheter therethrough; and (b) an introducer tube extending rom the handle and having (1) a bore therethrough aligned with and communicating with the groove for receiving a guidewire and selected catheter, and (2) an outer diameter selected for releasably mounting the antimicrobial cuff assembly thereon;

threading a catheter of selected size through the introducer groove and tube and cuff assembly, leaving the introducer above the skin entry point and advancing the catheter over the wire and through the introducer subcutaneously; and advancing the cuff assembly subcutaneously to position the antimicrobial cuff beneath the skin.

6. The method of claim 5, further comprising the step of separating the introducer from the catheter and cuff by pivoting the catheter and introducer away from one another and withdrawing the introducer from the catheter and cuff.

7. A method according to claim 5 or 6 wherein said cuff has tissue in-growth properties.

* * * * *